United States Patent
Heigl et al.

(10) Patent No.: US 7,711,083 B2
(45) Date of Patent: May 4, 2010

(54) METHOD FOR RECONSTRUCTING A THREE-DIMENSIONAL IMAGE VOLUME AND X-RAY DEVICES

(75) Inventors: Benno Heigl, Coburg (DE); Stefan Hoppe, Amberg (DE); Joachim Hornegger, Effeltrich (DE); Ernst-Peter Rührnschopf, Erlangen (DE); Holger Scherl, Bad Hersfeld (DE); Bernhard Scholz, Heroldsbach (DE); Michael Zellerhoff, Forchheim (DE)

(73) Assignee: Siemens Aktiengesellschaft, Munich (DE)

( * ) Notice: Subject to any disclaimer, the term of this patent is extended or adjusted under 35 U.S.C. 154(b) by 328 days.

(21) Appl. No.: 11/897,348

(22) Filed: Aug. 30, 2007

(65) Prior Publication Data

US 2008/0089468 A1 Apr. 17, 2008

(30) Foreign Application Priority Data

Sep. 1, 2006 (DE) ................ 10 2006 041 033

(51) Int. Cl.
*A61B 6/00* (2006.01)
(52) U.S. Cl. ............................ 378/20; 378/4
(58) Field of Classification Search ............... 378/4, 378/20–22
See application file for complete search history.

(56) References Cited

U.S. PATENT DOCUMENTS

| | | | | |
|---|---|---|---|---|
| 4,361,899 | A | * | 11/1982 | Amplatz ................ 378/21 |
| 5,119,408 | A | | 6/1992 | Little et al. |
| 5,305,368 | A | * | 4/1994 | Bisek et al. ................ 378/146 |
| 5,319,693 | A | | 6/1994 | Eberhard et al. |
| 5,740,224 | A | * | 4/1998 | Muller et al. ................ 378/11 |
| 5,838,765 | A | * | 11/1998 | Gershman et al. ........... 378/196 |
| 6,236,704 | B1 | | 5/2001 | Navab et al. |
| 2004/0179643 | A1 | | 9/2004 | Gregerson et al. |
| 2005/0074087 | A1 | * | 4/2005 | Nukui ...................... 378/7 |
| 2008/0226021 | A1 | * | 9/2008 | Holt ......................... 378/14 |

FOREIGN PATENT DOCUMENTS

DE 100 30 633 A1 1/2001

OTHER PUBLICATIONS

Alexander Katsevich; "Image reconstruction for the circle-and-arc trajectory"; Physics in Medicine and biology, Phys. Med. Biol; Apr. 27, 2005; pp. 2249-2265; vol. 50; Institute of Physics Publishing, IOP Publishing Ltd., United Kingdom.

(Continued)

*Primary Examiner*—Edward J Glick
*Assistant Examiner*—Alexander H Taningco

(57) ABSTRACT

To enable an artifact free reconstruction even in the case of large regions of interest and with scanning paths of below 360°, provision is made for a method, with which a three-dimensional image volume is reconstructed from a number of two-dimensional projection images of a region of interest, which were recorded about the region of interest during a rotation of a recording system, comprising an x-ray source with a focal point and a detector, by calculating the gray scale values of the voxels of the image volume by back projection of the projection images, with which each two-dimensional projection images is composed in each instance from at least two individual projection images to form an extended two-dimensional projection image, with the respectively at least two individual projection images being recorded with a constant relative position between the focal point and the region of interest.

20 Claims, 10 Drawing Sheets

OTHER PUBLICATIONS

J. Pack, F. Noo; "Cone-Beam Reconstruction Using 1D Filtering Along the Projection of M-Lines"; Inverse Problems; Apr. 2005; pp. 1105-1120; vol. 21.

J. Pack, F. Noo, R. Clackdoyle; "Cone Beam Reconstruction Using the Back Projection of Locally Filtered Projections"; IEEE Transactions on Medical Imaging; Jan. 2005; pp. 70-85; vol. 14, No. 1.

E.Y. Sidky, Y. Zou, X. Pan; "Minimum Data Image Reconstruction Algorithms with Shift-Invariant Filtering for Helical, Cone-Beam CT"; Physics in Medicine and Biology; 2005; pp. 1643-1657; vol. 50.

L. Yu, D. Xia, Y. Zou, X Pan, C. Pelizzari, P. Munro; "Region of Interest Reconstruction from Truncated Data in Circular Cone-Beam CT"; Proceedings of the SPIE; 2005; pp. 412-418; vol. 5747.

E.Y. Sidky, Y. Zou, X-Pan; "A Minimum Data FBP-Type Algorithm for Image Reconstruction in Cone beam CT"; Eighth International Meeting on Fully Three-Dimensional Image Reconstruction in Radiology and Nuclear Medicine, Salt Lake City, Utah; Jul. 6-9, 2005.

V. Liu, N.R. Lariviere, G. Wang; X-ray Micro-CT with a Displaced Detector Array: Application to helical cone-beam reconstruction:; Medical Physics, Oct. 2003; pp. 2758-2761, vol. 30, No. 10.

P.S. Cho, A.D. Rudd, R.H. Johnson; "Cone-Beam CT from Width Truncated Projections"; Computerized Medical Imaging and Graphics; 1996; pp. 49-57; vol. 20, No. 1.

L.A. Feldkamp, L.C. Davis and J.W. Kress; "Practical Cone-Beam Algorithm"; J. Opt. Soc Am. A. Jun. 1984; pp. 612-619; vol. 1, No. 6.

* cited by examiner

METHOD FOR RECONSTRUCTING A THREE-DIMENSIONAL IMAGE VOLUME AND X-RAY DEVICES

CROSS REFERENCE TO RELATED APPLICATIONS

This application claims priority of German application No. 10 2006 041 033.5 filed Sep. 1, 2006, which is incorporated by reference herein in its entirety.

FIELD OF THE INVENTION

The invention relates to a method for reconstructing a three-dimensional image volume from two-dimensional projection images of an object as well as an x-ray device for implementing a method of this type and a further x-ray device for implementing a method of this type as claimed in the claims.

BACKGROUND OF THE INVENTION

With the current three-dimensional cone beam reconstruction with the aid of C-arm systems, the so-called Wide Object Problem arises during the examination of certain body regions (such as for instance abdomen or breast), which exceed a maximum width determined by the recording geometry (detector dimension and focal length). A decisive processing step for 3D reconstruction using filtered back projection is the filtering of the projection data along lines, which run horizontally or approximately horizontally in the detector.

As a result of the non-local nature of the filter core (such as ramp filters or Hilbert filters for instance), the filter lines must pass through the whole projection of the examination area and may not herewith be truncated, even if only one part of the region of interest (ROI) is to be reconstructed. In many recordings, the limited detector width however results in transaxially truncated projections of the region of interest, since this cannot be completely covered by the field of view (FoV). The said field of view results in truncated filter lines in these projections. The results are significant reconstruction artifacts, such as for instance so-called truncation artifacts, which distort the result and hinder, complicate or render impossible the qualified diagnosis thereof.

The so-called Wide Object Problem relates to almost all current reconstruction algorithms, which operate on the basis of filtered back projection (FBP algorithms), and that is the vast majority. This applies in particular to the Feldkamp algorithm, which is designed for a circular scanning path of the focal point and is known from L. A. Feldkamp, L. C. Davis, J. W. Kress: Practical Cone-Beam Algorithm, J. Opt. Soc. Am. A, Vol. 1, No. 6, pages 612-619. More recent precise reconstruction methods (such as for instance known from A. Katsevich: "Image Reconstruction for the Circle and Arc Trajectory", Physics in Medicine and Biology, Vol. 50, pages 2249-2265, April 2005 and from J. Pack, F. Noo: "Cone-Beam Reconstruction Using ID Filtering Along the Projection of M-Lines", Inverse Problems, Vol. 21, pages 1105-1120, April 2005) require extended path curves for scanning (such as circle and line, circle and circle arc), but nevertheless feature this problem. A stable solution for the Wide Object Problem would thus constitute an important and central contribution to solving reconstruction problems in computed tomography.

Back projection filtration (BPF) methods, which only implement filtering in the object space following back projection and only allow local calculation steps on the projection data, can cope with truncated projections up to a certain degree. This has been demonstrated using the example of a helix-shaped (J. Pack, F. Noo, R. Clackdoyle: "Cone Beam Reconstruction Using the Back projection of Locally Filtered Projections" IEEE Transactions on Medical Imaging, Vol. 24, No. 1, pages 70-85, January 2005; E. Y. Sidky, Y. Zou, X. Pan: "Minimum Data Image Reconstruction Algorithms with Shift-Invariant Filtering for Helical, Cone-Beam CT" Physics in Medicine and Biology, Vol. 50, pages 1643-1657, 2005) and a circular (L. Yu, D. Xia, Y. Zou, X. Pan, C. Pelizzari, P. Munro: "Region of Interest Reconstruction from Truncated Data in Circular Cone-Beam CT", Proceedings of the SPIE, Vol. 5747, pages 412-418, 2005) path curve for scanning for cone beam reconstruction. In some instances, the BPF approach solves the problem of truncated projections and enables an artifact-free reconstruction of an ROI within the examination area.

Furthermore, a FBP method derived from the BPF approach is known (E. Y. Sidky, Y. Zou, X-Pan: "A Minimum Data FBP-Type Algorithm for Image Reconstruction in Cone-Beam CT", Eighth International Meeting on Fully Three-Dimensional Image Reconstruction in Radiology and Nuclear Medicine, Salt Lake City, Utah, Jul. 6-9, 2005), which comprises similar characteristics. The region of interest is however limited to the field of view (FoV), so that even with this method, it is frequently not possible to reconstruct the complete region of interest (such as for instance abdomen of a large patient).

Methods also exist however, which enlarge the field of view (FoV). By way of example, reference is made here to the detector displacement method, in which the detector is no longer arranged symmetrically in respect of the optical axis, but instead with a certain displacement (V. Liu, N. R. Lariviere, G. Wang: "X-ray Micro-CT with a Displaced Detector Array: Application to helical cone-beam reconstruction", Medical Physics, Vol. 30, No. 10, pages 2758-2761, October 2003). The detector displacement method however requires a circular or helical path curve for scanning over an angular range of at least 360 degrees. Furthermore, with cone-beam geometry, this method represents an approximate field of view (FoV) enlargement and thus results in artifacts in the event of large cone angles.

A similar approach is the extrapolation of truncated projection data. In P. S. Cho, A. D. Rudd, R. H. Johnson, "Cone-Beam CT from Width-Truncated Projections", Computerized Medical Imaging and Graphics, Vol. 20, No. 1, pages 49-57. 1996) the missing line integrals are expanded based on approximate assumptions (such as for instance the quasi redundancy of opposite beams, with the cone angle being ignored). This method also requires a path curve of 360° for scanning. In particular, the last-mentioned method is understood as an extension of the FDK algorithm.

SUMMARY OF THE INVENTION

The object of the present invention is to provide a method for reconstructing a three-dimensional image volume from two-dimensional projection images of a region of interest, which also enables an artifact-free reconstruction in the case of large regions of interest and also in the case of scanning paths below 360°. Furthermore, the object of the invention is to provide an x-ray device which is suited to implementing the method.

The object is achieved in accordance with the invention by a method for reconstructing a three-dimensional image volume from two-dimensional projection images of a region of interest and by an x-ray device and by an x-ray device as claimed in the independent claims. Advantageous embodiments of the invention are the subject matter of associated subclaims in each instance.

With the method according to the invention, the limited detector surface and thus the limited field of view (FoV) can be extended, by producing two (or more) individual projection images which differ from one another and which can be combined to form an extended projection image. The overall region of interest (ROI) can herewith be displayed.

The respectively at least two individual projection images are recorded with a constant relative position between the focal point and the region of interest. A constant relative position is herewith understood to mean that a triangle, which is spanned by two points in the region of interest and the focal point, has a constant size.

The respectively at least two individual projection images are also such that the respective x-ray beams for illuminating the at least two individual projection images can be combined to form a continuous, extended x-ray which covers the region of interest.

According to a first alternative of the invention, the respectively at least two individual projection images differ in respect of an angle of rotation, through which the recording system is rotated about the focal point or about an axis of rotation through the focal point, while the focal point and the region of interest are fixed. In order to record the two-dimensional projection images, the recording system thus not only rotates about a first rotation center, which is generally positioned in the region of interest in order thus to provide a projection image for different curve points of the focal point, but a second rotation center additionally exists in the x-ray source, in particular in its focal point, so that at least two individual projection images can be recorded for each curve point.

The region is herewith extended in a simple and uncomplicated manner, said region being mapped from all curve points of the scanning path curve in two-dimensional projection images, thereby also enabling it to be reconstructed without artifacts and in a three-dimensional manner. The scanning path curve or trajectory is herewith defined by the path of the x-ray focus.

Two (or more) individual projection images are produced at each curve point of the trajectory. The difference between the individual recordings thus consists in the recording system capturing different angles of rotation about the x-ray source, in particular the focal point of the x-ray source. The rotation of the recording system comprising the x-ray source and x-ray detector about the x-ray source thus allows the acquisition of additional image information from the x-rays.

A homographic relation herewith results between the individual projection images, said homographic relation being able to be used to combine the individual projection images to form a large extended projection image by means of rectification. This applies both to fan beam geometry as well as to cone beam geometry. In this way, the detector is extended virtually, partially up to a multiple of its actual width. The FoV thus enlarged allows the relevant body regions to be captured in their entirety.

Homography is herewith a mapping regulation, by means of which points are transferred from a 2D coordinate system to another 2D coordinate system. A homographic relation thus always exists between the corresponding intersection points of the different planes, whenever two or more planes intersect a beam bundle. If the points are expressed in homogenous coordinates, this relation can be formulated as a linear mapping $x'=H'x$, with x designating the original point, $x'$ the transformed point and the 3×3 matrix $H'$ designating the homographic transformation itself. The combination of the at least two individual projection images can herewith also be referred to as the setting up of a virtual detector which is extended in relation to the actual x-ray detector. This applies irrespective of the alternative of the invention, according to which the two or more individual projection images are recorded.

According to a second alternative of the invention, the respectively at least two individual projection images differ in respect of an angle of rotation, through which the region of interest is rotated about the focal point or about an axis of rotation through the focal point, while the focal point and the recording system are fixed.

According to a third alternative of the invention, the respectively at least two individual projection images differ in that both the focal point and the region of interest are positioned differently in respect of each other with a constant relative position and the recording system is rotated about the focal point or about an axis of rotation through the focal point.

The method according to the invention and/or its alternative embodiments on the one hand enable the complete artifact-free reconstruction of larger body regions such as the abdomen or breast, which was hitherto not possible by virtue of the limited detector surface. On the other hand, during reconstruction of the region of interest, in which only a part of the entire body region is reconstructed, it is possible to prevent truncated projection images from resulting in serious reconstruction artifacts. Moreover, the method according to the invention can be expediently combined with all reconstruction algorithms, with which truncated projection images cause artifacts, and is to be understood as an extension hereof. This applies in particular to the algorithm by Feldkamp, Davis and Kress, which is used as standard in current C-arm systems, since this comprises horizontal filter lines in the case of a circular scanning path (trajectory).

A decisive advantage with the combination of the method according to the invention with known (approximate or precise) reconstruction algorithms is that these do not need to be modified here. The virtual detector can be set up as a preprocessing step, in other words the extended projection images used for the reconstruction are composed from two or more individual projection images prior to the actual reconstruction and are subsequently used for the reconstruction. Only the recording protocol, in other words the recording sequence of the individual projection images, has to be modified accordingly. In addition, the method according to the invention is suited to flat as well as curved detectors and can be used both with fan beam geometry and also with cone beam geometry.

For an uncomplicated method, precisely two individual projection images are advantageously created in each instance and are combined to form an extended projection image.

According to one embodiment of the invention, the respective angles of rotation of the at least two individual projection images are arranged in a plane. This ensures that the combination of the projection images to form the extended projection image is facilitated.

For a simple combination of the at least two individual projection images, it is advantageous for the rotation of the recording system or the region of interest about the focal point or an axis of rotation through the focal point to lie essentially in the rotation plane of the recording system about the region of interest, which is equivalent to a rotation (tilting) about an axis of rotation, which runs orthogonal to the rotation plane of the recording system about the region of interest through the focal point. It has herewith proven particularly advantageous if a first projection image is recorded with a first angle of rotation of the recording system about the focal point or about an axis of rotation through the focal point and a second projection image is recorded with a second angle of rotation of the recording system about the focal point or about an axis of rotation through the focal point, with the first angle of rotation corresponding to the negative second angle of rotation. The reference point here is a center position, which is herewith defined such that a perpendicular from the focus of the x-ray source onto the x-ray detector intersects the axis of rotation of the recording system.

According to a further embodiment of the invention, the individual projection images to be combined in each instance feature an overlap relative to one another of more than 0% and less than 50%, in particular less than 10%. An overlap of more than 0% facilitates a combination of the individual projection images, since adjustment and smoothing can be carried out in the event of discontinuity or deviations with the aid of twice-measured pixels. At the same time, an overlap of less than 50% and in particular less than 10% prevents a patient being exposed to unnecessary radiation.

A further embodiment of the invention provides that an overlap is adjusted as a function of the object, in particular its size. This enables the x-rays to be used particularly effectively if as few x-rays as possible radiate in an unused fashion past the object, depending on the height and width of said object.

For the recording sequence of individual projection images with regard to different curve points, two advantageous embodiments are in turn possible. According to a first embodiment, the recording sequence of the projection images is such that during a first rotational pass of the recording system about the region of interest all the first individual projection images are recorded and subsequently during a second rotational pass of the recording system about the region of interest all the second individual projection images are recorded, with each first projection image being combined with a second projection image in each instance.

According to a second embodiment, the recording sequence of the projection images is such that the respectively at least two individual projection images, which are combined to form an extended two-dimensional projection image in each instance, are recorded in each instance in direct sequence during a single rotational pass of the recording system about the region of interest.

An x-ray device which is suited to implementing the method according to the invention in the first alternative comprises a recording system, containing a radiation source and an x-ray detector, for recording two-dimensional projection images of a region of interest, with the recording system being rotatable about a first rotation center between the radiation source and the x-ray detector and about a second rotation center in the focal point of the radiation source or about an axis of rotation through the focal point of the radiation source, and a control and computing unit for reconstructing a three-dimensional image volume from the two-dimensional projection images.

An x-device which is suited to implementing the method according to the invention in the second alternative comprises a recording system, containing a radiation source and an x-ray detector, for recording two-dimensional projection images of a region of interest, with the recording system being rotatable about a first rotation center between the radiation source and the x-ray detector, a couch for supporting the region of interest which can be adjusted in a spatially three-dimensional manner, and is in particular rotatable about the focal point, and a control and computing unit for reconstructing a three-dimensional image volume from the two-dimensional projection images.

A similar x-ray device to that used to implement the second alternative is suited to implementing the method according to the invention in the third alternative, with the couch not being rotatable about the focal point, but instead only having to be displaceable in a two-dimensional manner in the rotation plane of the recording system.

The method according to the invention is particularly advantageously executed with an x-ray device, with which the recording system is arranged on an industrial robot and/or articulated arm robot directly or by means of a bracket or with which the couch is arranged on an industrial robot and/or articulated arm robot. Such an x-ray device enables any movements in the space to be carried out in a simple fashion.

BRIEF DESCRIPTION OF THE DRAWINGS

The invention as well as further advantageous embodiments according to features of the subclaims are described in more detail below with reference to schematically illustrated exemplary embodiments, without herewith restricting the invention to these exemplary embodiments, in which:

DETAILED DESCRIPTION OF THE INVENTION

Figure 1:
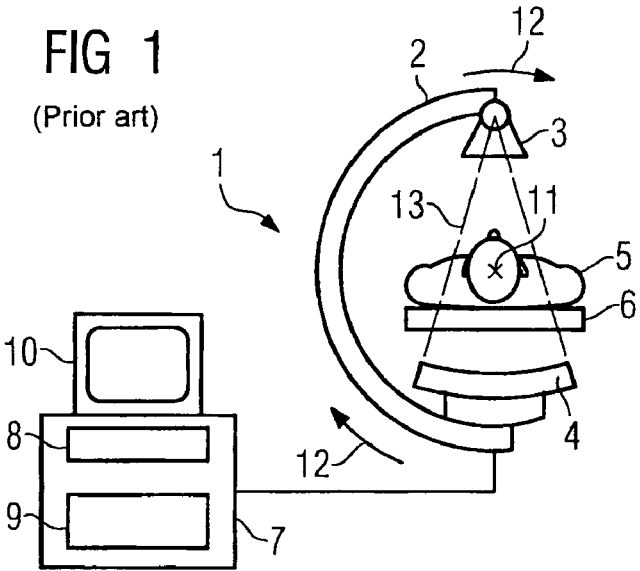
FIG. 1 shows a plan view of a C-arm x-ray system according to the prior art

FIG. 1 shows a schematic representation of a C-arm x-ray system 1, which comprises a C-arm 2, to which an x-ray source 3 and an x-ray detector 4 disposed opposite to each other are attached, generally in fixed alignment. The x-ray detector 4 can be a flat or curved x-ray detector 4 based on a solid body for instance. Such an x-ray detector 4 can comprise a scintillator for instance and a detector matrix with pixel elements. The x-ray source 3 generates an x-ray beam 13. The C-arm can be rotated (angled) about a region of interest 5 which is located on a patient bed 6, for instance by rotation about a first rotation axis 11 in the direction of the arrow 12 for instance. In this process, 2D projection images are recorded for different angular positions from the respective projection directions of the recording system. The region of interest 5 is arranged here such that its center point lies on the axis of rotation 11.

The 2D projection images thus obtained are forwarded to a control and computing unit 7, which comprises at least a data memory unit 8 and a computing module 9 with a processor or suchlike. Reconstruction of the projection images to 3D volumes is carried out in the control and computing unit for instance according to a known method by means of filtered back projection or back projection and filtering. The recorded projection images as well as the optionally reconstructed image volumes can be observed on a screen 11.

Figure 2:
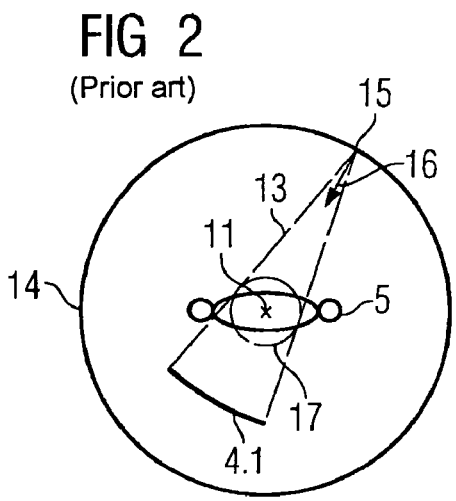
FIG. 2 shows a geometry of a truncated projection of a patient using a curved x-ray detector
Figure 3:
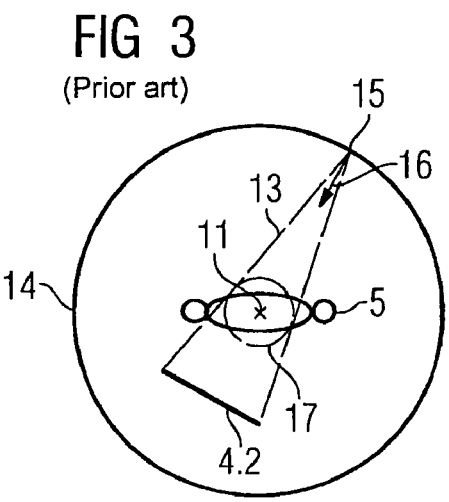
FIG. 3 shows a geometry of a truncated projection of a patient using a flat x-ray detector

FIG. 2 and FIG. 3 show the problem of truncated projections of the region of interest 5 with a method for reconstructing a three-dimensional image volume from two-dimensional projection images of a region of interest according to the prior art using the example of a curved x-ray detector 4.1 and a flat x-ray detector 4.2 respectively. This problem means that an artifact-free reconstruction of 3D volumes of the region of interest 5 to be mapped is not possible by virtue of truncated filter lines. The x-ray beam 13 passes through the region of interest 5 from a focal point 15 of the x-ray source 3 in radiation direction 16 and strikes the x-ray detector 4. In this way the path curve 14 describes the trajectory of the focal point 15 during a complete rotation of the C-arm 2 through 360°. Parts of the region of interest 5 are not captured from each curve point of the path curve 15 by the x-ray beam 13, but are instead truncated for some curve points. The projection center 17 herewith designates the regions, which are captured by the x-ray beam 13 at each arbitrary curve point.

Figure 13:
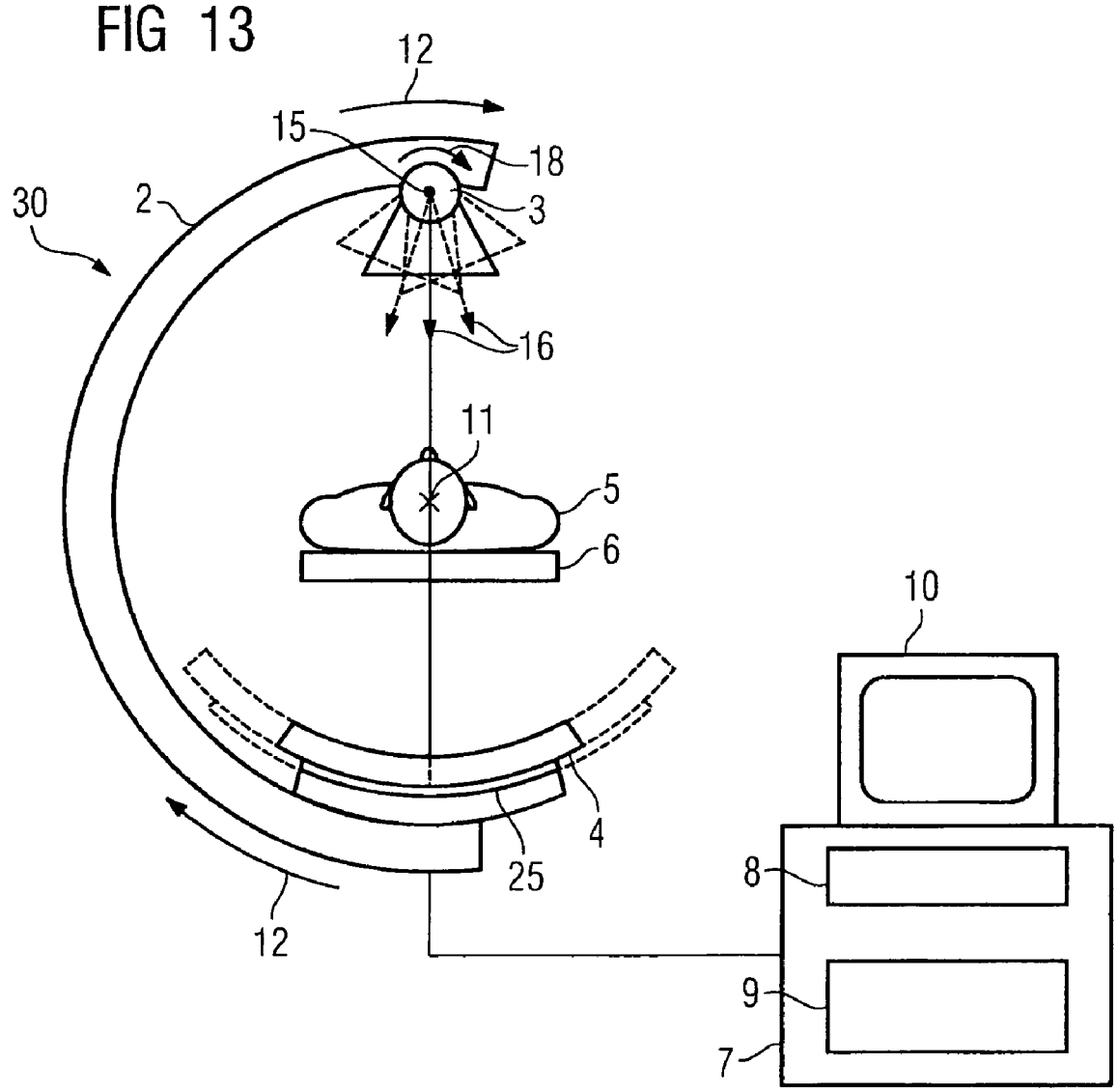
FIG. 13 shows an x-ray system according to the invention with a rotatable C-arm and a rotatable recording system
Figure 14:
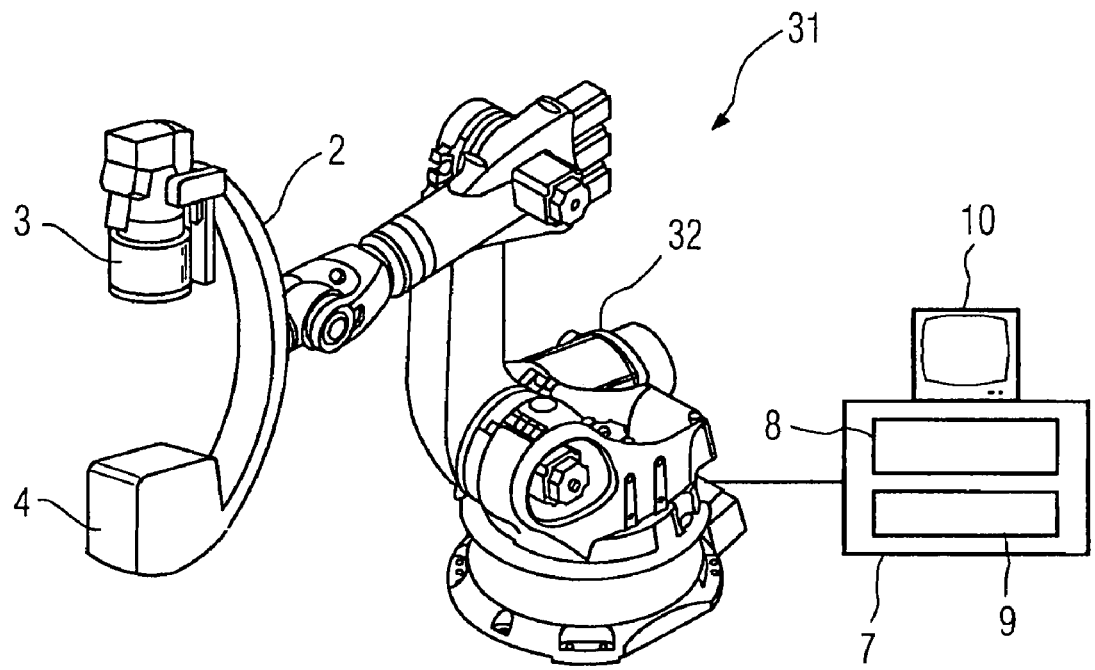
FIG. 14 shows a further x-ray system according to the invention with an articulated arm robot

The first alternative of the method according to the invention is clarified with the aid of FIG. 4 to FIG. 12. With this alternative, the two or more individual projection images to be combined are recorded on the scanning path 14 with a fixed position of the focal point 15. FIG. 13 and FIG. 14 show two x-ray devices which are suited to implementing the method in the first alternative.

FIG. 4 to FIG. 7 show the virtual extension of the x-ray detector, which is used for the method according to the invention, to form a virtually extended detector 20, by combining two individual projection images, which differ in respect of an angle of rotation of the recording system about the x-ray source 3 and in particular the focal point 15 of the x-ray source 3, to form an extended projection image for a specific curve point. The examples of the curved x-ray detector 4.1 (FIGS. 4 and 6) and of the flat x-ray detector 4.2 (FIGS. 5 and 7) are shown here in a similar manner to FIG. 2 and FIG. 3. The respective x-ray detector 4 and the x-ray source 3 are aligned in a fixed manner relative to one another.

Figure 4:
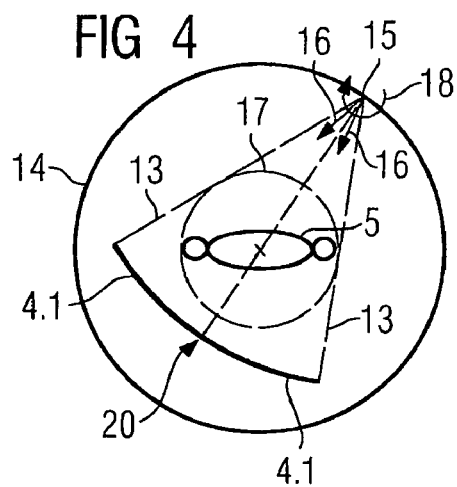
FIG. 4 shows a geometry of an extended projection composed according to the invention from two adjacent projections using a curved x-ray detector
Figure 5:
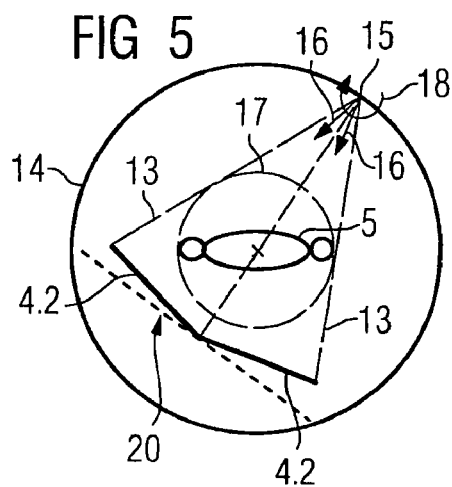
FIG. 5 shows a geometry of an extended projection composed according to the invention from two adjacent projections using a flat x-ray detector

FIG. 4 shows the recording system comprising the x-ray source 3 and the curved x-ray detector 4.1 for a specific curve point in two positions which differ in respect of the angle of rotation of the recording system about the focal point 15 of the x-ray source 3. The rotation of the recording system about the focal point 15 of the x-ray source 3 takes place for instance in the second direction of rotation 18. The respective projection direction 16 of the recording system is shown by the corresponding arrows. With the method according to the invention, a projection image is recorded for each of the two projection directions 16 of the recording system, said projection images then being combined to form an extended projection image.

With a suitable selection of the respective projection directions 16 of the recording system, the virtual extension of the x-ray detector 4 enables the region of interest 5 to be completely captured in the projection center 17 from each curve point of the path curve 14 using the extended x-ray beam which is composed of the two x-ray beams 13, so that truncated projections no longer exist. More than two projection images can also be combined to form an extended projection image.

Figure 12:
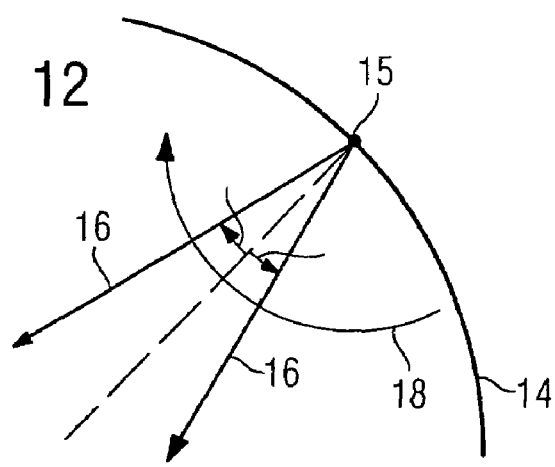
FIG. 12 shows a cutout from a path curve with two projection directions of the recording system having different angles of rotation

FIG. 12 shows an enlarged view of the rotation of the recording system about the focal point 15 of the x-ray source 3 in the second rotation direction 18 and the respective projection directions 16 of the recording system with their different angles of rotation, a first angle of rotation a of the recording system and a second angle of rotation β of the recording system. It is herewith particularly advantageous if the first angle of rotation α of the recording system is identical to the negative second angle of rotation β with regard to the center position (shown with a dashed line in FIG. 12).

Figure 6:
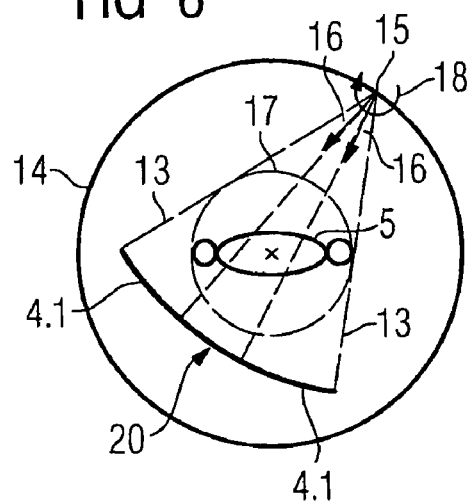
FIG. 6 shows a geometry of an extended projection composed according to the invention from two overlapping projections using a curved x-ray detector
Figure 7:
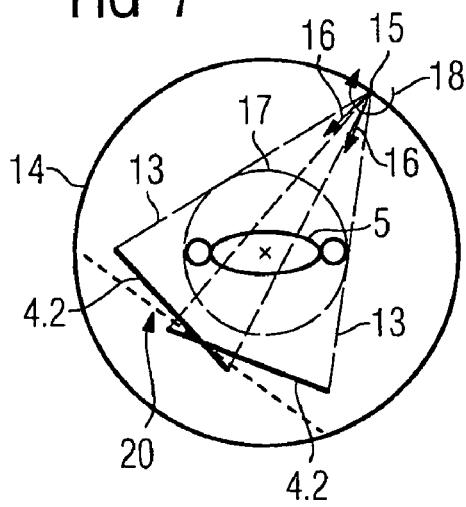
FIG. 7 shows a geometry of an extended projection composed according to the invention from two overlapped projections using a flat x-ray detector

In contrast to FIG. 6, FIG. 4 shows the case of two individual projection directions 16 of the recording system, with which the x-ray beams 13 do not or barely overlap, but instead adjoin flush with one another. In a case of this type, a particularly large region of interest can be mapped and combination of the individual projection images to form an extended projection image is facilitated. In FIG. 6, the projection directions 16 of the recording system are selected such that the individual projection images overlap. This is expedient for instance for the calibration of actual path curves with the aid of image processing algorithms. During reconstruction, the overlap region can once again be reduced to zero by suitable collimation, in order to maintain a low radiation dose.

In a similar manner to FIG. 4 and FIG. 6, FIG. 5 and FIG. 7 show the case of a flat x-ray detector 4.2. In this case, the individual projection images must be combined with a rectification. In contrast to a curved x-ray detector 4.1, which allows a uniform resolution in the combined projection image, it must be noted and included in an evaluation that the resolution in the extended projection image reduces towards the edges when a flat detector is used.

With the method according to the invention for reconstructing a three-dimensional image volume, the gray scale values of the voxels of the image volume are calculated by back projection of the extended projection images. Any known reconstruction algorithm can be used for this purpose, for instance the Feldkamp algorithm. Use of the extended projection images allows the reconstructable region to be significantly enlarged, so that large body regions can also be displayed in a three-dimensional manner without artifacts.

Figure 8:
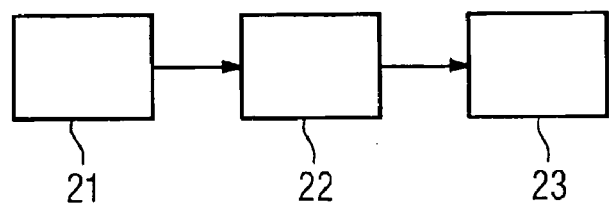
FIG. 8 shows a method according to the invention for reconstructing a three-dimensional image volume from combined projection images

FIG. 8 shows the method according to the invention from a first step 21, a second step 22 and a third step 23. In the first step 21, two projection images are recorded and stored in each instance for different curve points, according to the first alternative for instance, with the two projection images differing in respect of the angle of rotation of the recording system about the focus of the x-ray source. In the second step 22, the two projection images for each curve point are combined to form an extended projection image. This can be carried out for instance in the control and computing unit 7. In a third step 23, a reconstruction of the three-dimensional image volume of the patient is then carried out from the extended two-dimensional projection images according to a known reconstruction algorithm. This can likewise be carried out in the control and computing unit 7.

Figure 9:
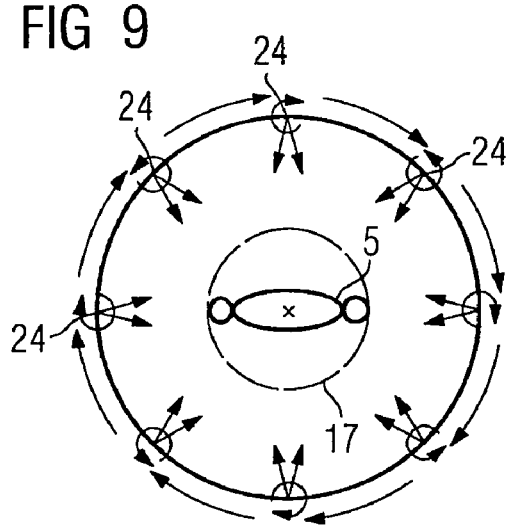
FIG. 9 shows a recording protocol for circular curve paths for recording projection images
Figure 10:
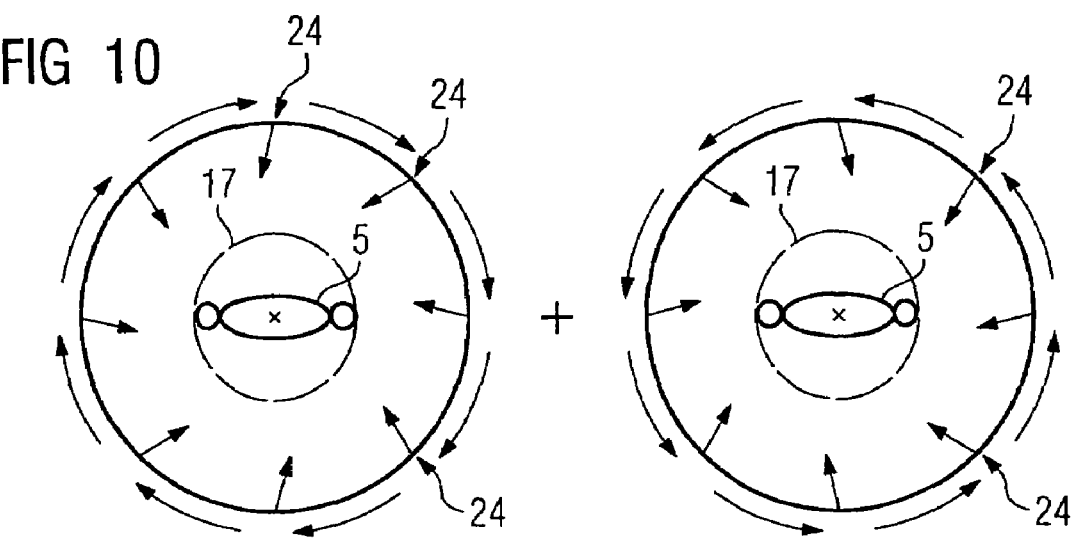
FIG. 10 shows a further recording protocol for circular curve paths for recording projection images
Figure 11:
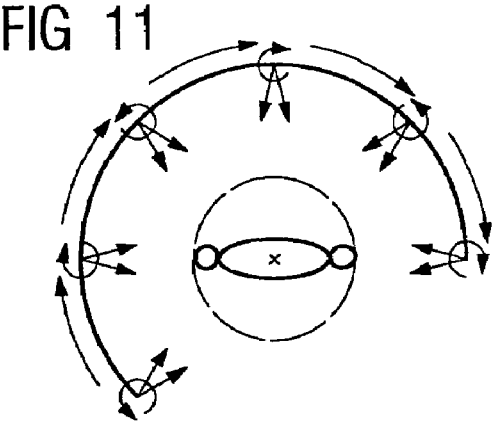
FIG. 11 shows a further recording protocol for circular curve paths for recording projection images

FIG. 9 to FIG. 11 show different possible recording protocols for circular curve paths for recording the different two-dimensional projection images. FIG. 9 shows a recording protocol, with which, during rotation of the recording system through 360° about the region of interest 5, eight curve points 24 are approached one after the other in a single rotational pass for instance and a first and a second projection image is recorded in sequence at each curve point. To this end, a rotation of the recording system about the focal point of the x-ray source is necessary in each instance at each curve point. FIG. 11 shows a similar recording protocol to FIG. 9, with a rotation of the recording system about the region of interest through only 225° or less (such as e.g. short scan or super short scan) being carried out. The possibility of also being able to travel through partial circles advantageously distinguishes the method according to the invention compared with other approaches (such as for instance detector displacement).

FIG. 10 shows a recording protocol, with which, during rotation of the recording system through 360° about the region of interest 5, eight curve points 24 are approached one after the other in a first rotational pass for instance and a first projection image is recorded at each curve point. The recording system is then rotated about the focus of the x-ray source and all the curve points 24 are approached in reverse sequence in a second rotational pass and a second projection image is recorded at each curve point. The principle can be advantageously applied to further path curves (such as for instance helix, circle and line, circle and circle-arc).

An object-dependent overlap can then be adjusted for instance if the dimensions of the region of interest are at least approximately known. Provision can also be made for instance to determine the dimensions of the region of interest by means of one or a number of prerecordings using a low x-ray dose and to then adjust the overlap manually or automatically. The measured data can then be averaged in the overlap region of the projections, thereby resulting in a reduction of the standard deviation of the measured values and thus in a noise reduction.

As an embodiment of the invention, FIG. 13 shows a further C-arm x-ray device 20, which differs from the x-ray device 1 according to the prior art such that in addition to rotation of the C-arm 2 about the region of interest 5, the recording system consisting of the x-ray source 3 and the x-ray detector 4 can be rotated in a common manner about a second rotation center in the focus 15 of the radiation source 3. The recording system can preferably be rotated in the plane of the rotation of the C-arm 2.

In addition to the rest position, FIG. 13 shows two further positions, by way of a dashed line, in which the recording system is rotated in each instance through an angle >0° about the focus 15 of the x-ray source 3 in the C-arm plane. The control and computing unit 7 can be used to control the rotation. The x-ray source 3 can be fastened in a tiltable manner for instance and the x-ray detector 4 can be fastened to rails 25 in such a manner that it can be moved along said rails. Expedient use of the method according to the invention requires the recording system to be rotatable through at least 5° in both directions about the x-ray source 3. In a system of this type, it must be ensured that the x-ray source and x-ray detector maintain a constant distance from one another and exhibit an orientation which remains the same relative to one another. According to a further embodiment of the invention, a computed tomography x-ray device is provided, with which the recording system can be rotated about a second rotation center in the radiation source, in particular in the focus of the radiation source.

The method according to the invention can be advantageously applied both to x-rays in cone beam form, which are generated for instance by a C-arm x-ray device, as well as to x-rays in fan beam form, which are generated for instance by a computed tomography x-ray device.

As an embodiment of the invention, FIG. 14 shows a robot x-ray device 31, with which a C-arm 2 supporting the recording system is arranged on a so-called articulated arm robot 32. Such an articulated arm robot 32, which is used as standard in the industrial production of cars for instance, has six axes of rotation for instance, with the result that any movement is possible in the space. The control and computing unit 7 is used in turn to control the rotation of the recording system 7 about the focus 15 of the x-ray source 3. An operator for instance can thus transmit the height and width of the region of interest to the control and computing unit 7 and said control and computing unit 7 calculates the angle of rotation needed for the complete mapping of the region of interest. The control and computing unit 7 then controls the subsequent movement of the articulated arm robot 32 and the C-arm 2.

The robot x-ray device 31 enables angles of rotation not only in the rotation plane of the C-arm 2, but for instance also in a plane which runs perpendicular thereto or in further planes which intersect the perpendicular of the x-ray source to the x-ray detector in the center position, depending on which parts of the region of interest are to be recorded. It is generally advantageous for the angle of rotation of the at least two individual projections, which are then combined, to lie in a plane.

In the second alternative of the method according to the invention, the respectively at least two individual projection images differ in respect of an angle of rotation, through which the region of interest 5 is rotated about the focal point 15 or about an axis of rotation through the focal point 15, while the focal point 15 and the recording system are fixed. Two (or more) individual projection images are recorded, as with the first alternative, at each curve point of the focal point 15 and are then combined to form an extended projection image. For the different individual projection images, the region of interest 5 is rotated about the focal point 15 of the x-ray source 3, the relative position of the region of interest 5 remaining the same here relative to the focal point 15.

Figure 15:
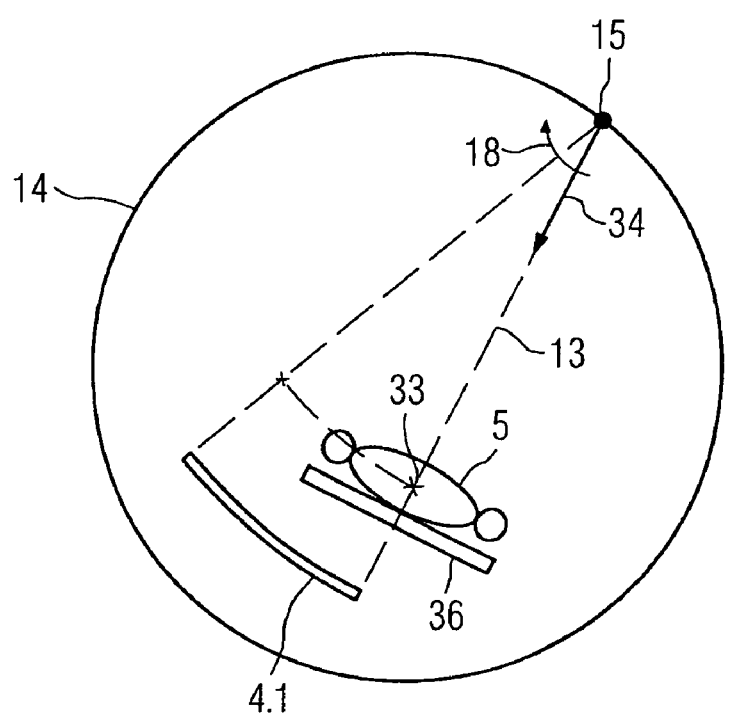
FIG. 15 shows a projection geometry in the case of a movement of the region of interest about the x-ray focus in its rotation plane, with the region of interest in a first position
Figure 16:
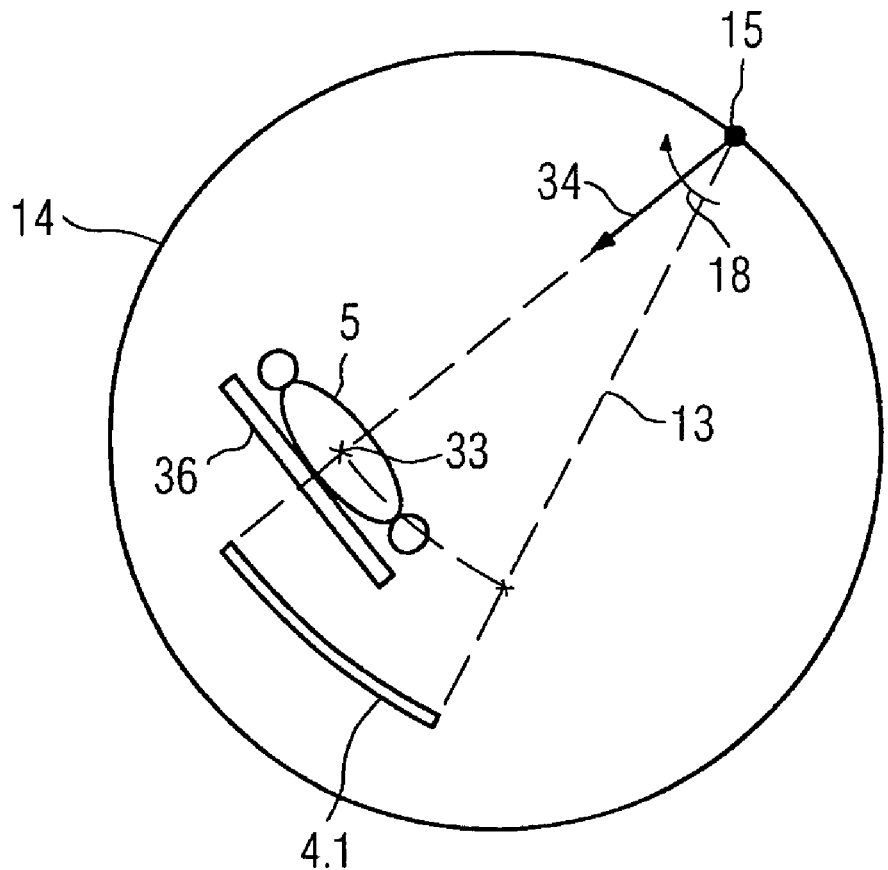
FIG. 16 shows a projection geometry in the case of a movement of the region of interest about the x-ray focus in its rotation plane, with the region of interest in a second position

FIG. 15 shows a first position of the region of interest 5, in which a first individual projection image is recorded and FIG. 16 shows a second position of the region of interest, in which a second individual projection image is recorded. In the case of the rotation of the region of interest 5 about the focal point 15, the respective angles of rotation relate to the projection direction 34 from the focal point 15 to the center point 33 of the region of interest 5. The perpendicular of the focal point 15 to the x-ray detector 4 can be used for instance as the angle of rotation zero point.

Figure 17:
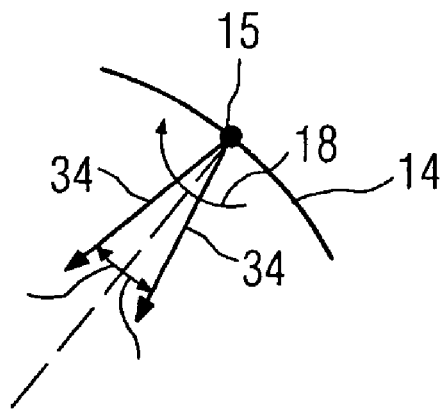
FIG. 17 shows a cutout from a path curve with two projection directions of the recording system with different angles of rotation of the region of interest

By way of example, FIG. 17 shows the two projection directions 34 from the focal point 15 to the center point 33 of the region of interest 5, with a first angle of rotation χ of the region of interest 5 occurring for instance in the first position of the region of interest 5 and a second angle of rotation δ of the region of interest 5 occurring in the second position for instance. The projection images are then combined and reconstructed as usual.

The rotational movement of the region of interest 5 about the focal point is effected by a couch, which can be adjusted in any manner in the space, for instance by a moveable patient bed 36. The moveability of the moveable patient bed 36 in the space, in other words with six degrees of freedom, is achieved for instance by an articulated arm robot, in particular one with 6 axles, on which the moveable patient bed 36 is arranged. It is worth noting that a patient is fastened to the moveable patient bed 36 as firmly as possible, as this rotates.

Also with this alternative of the method according to the invention, two individual projection images, with a rotation of the region of interest 5 about the focal point 15 therebetween, can either be recorded in an alternating manner within a rotational pass at each curve point or the respectively first projection image can be recorded first for all curve points in one rotational pass and after the rotation, the respectively second projection image can then be recorded for all curve points in a second rotational pass. Overlaps of the individual projection images can also be provided here.

In the third alternative of the invention, for the first individual projection image both the region of interest 5 as well as the recording system have a different position in comparison with the second individual projection image, with the relative position between the focal point 15 and the region of interest 5 being constant. In both positions the focal point 15 lies on the scanning path, however not at the same point, a connecting path 40 between the two positions of the focal point 15 being parallel to a connecting path 41 between the two positions of the center point 33 of the region of interest 5 and having the same length. The same applies to further individual projection images, if more than two are combined.

Figure 18:
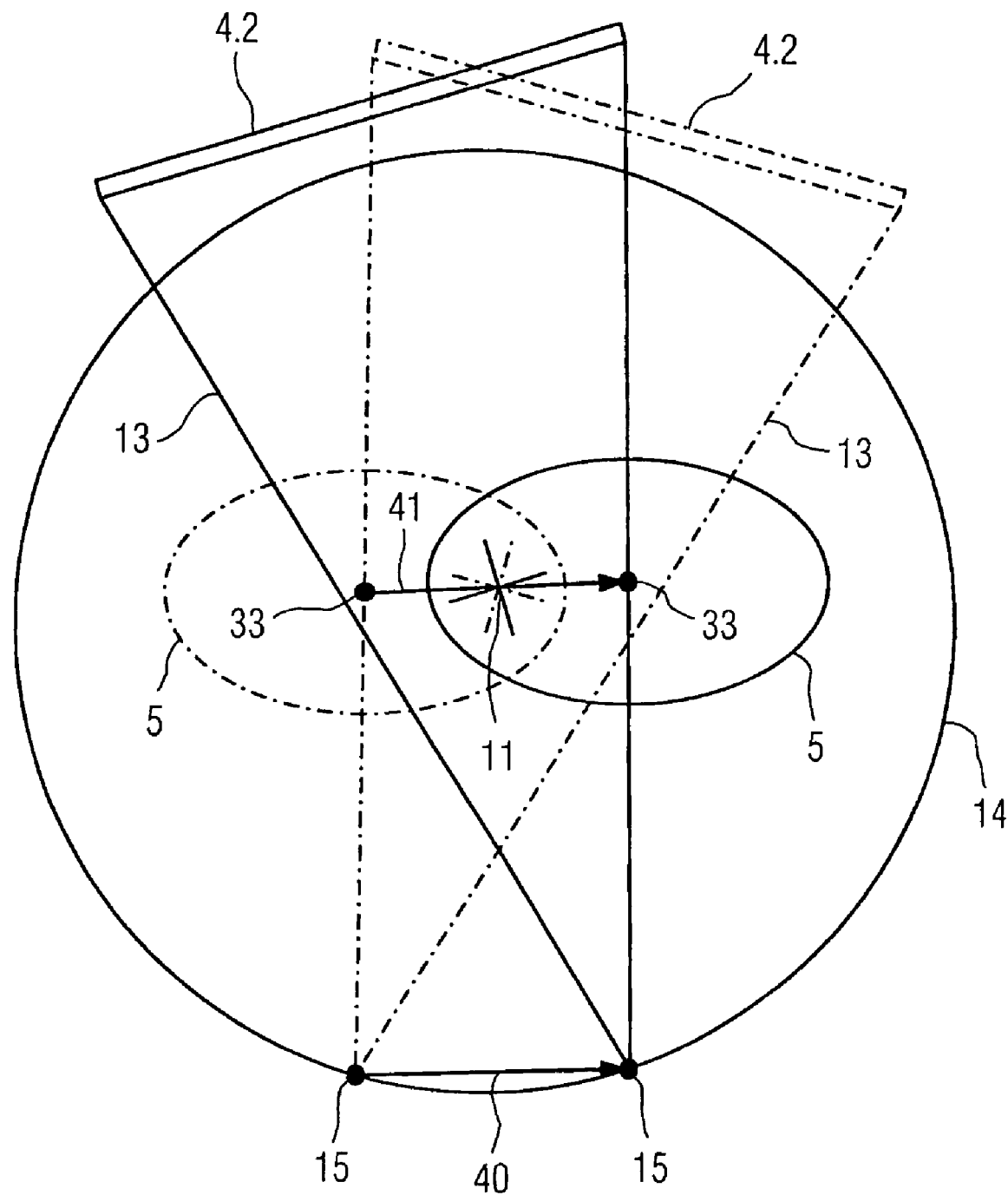
FIG. 18 shows a projection geometry in the case of a movement both of the region of interest and also of the recording system between two individual projection images to be combined

FIG. 18 shows the region of interest 5 and the recording system, shown by the focal point 15 and by way of example the flat x-ray detector 4.2, in a first position (solid line), in which the first individual projection image is recorded and in a second position (dashed line), in which the second individual projection image is recorded, with the first and the second individual projection images then being combined to form an extended projection image and being reconstructed as usual together with the further extended projection images.

Figure 19:
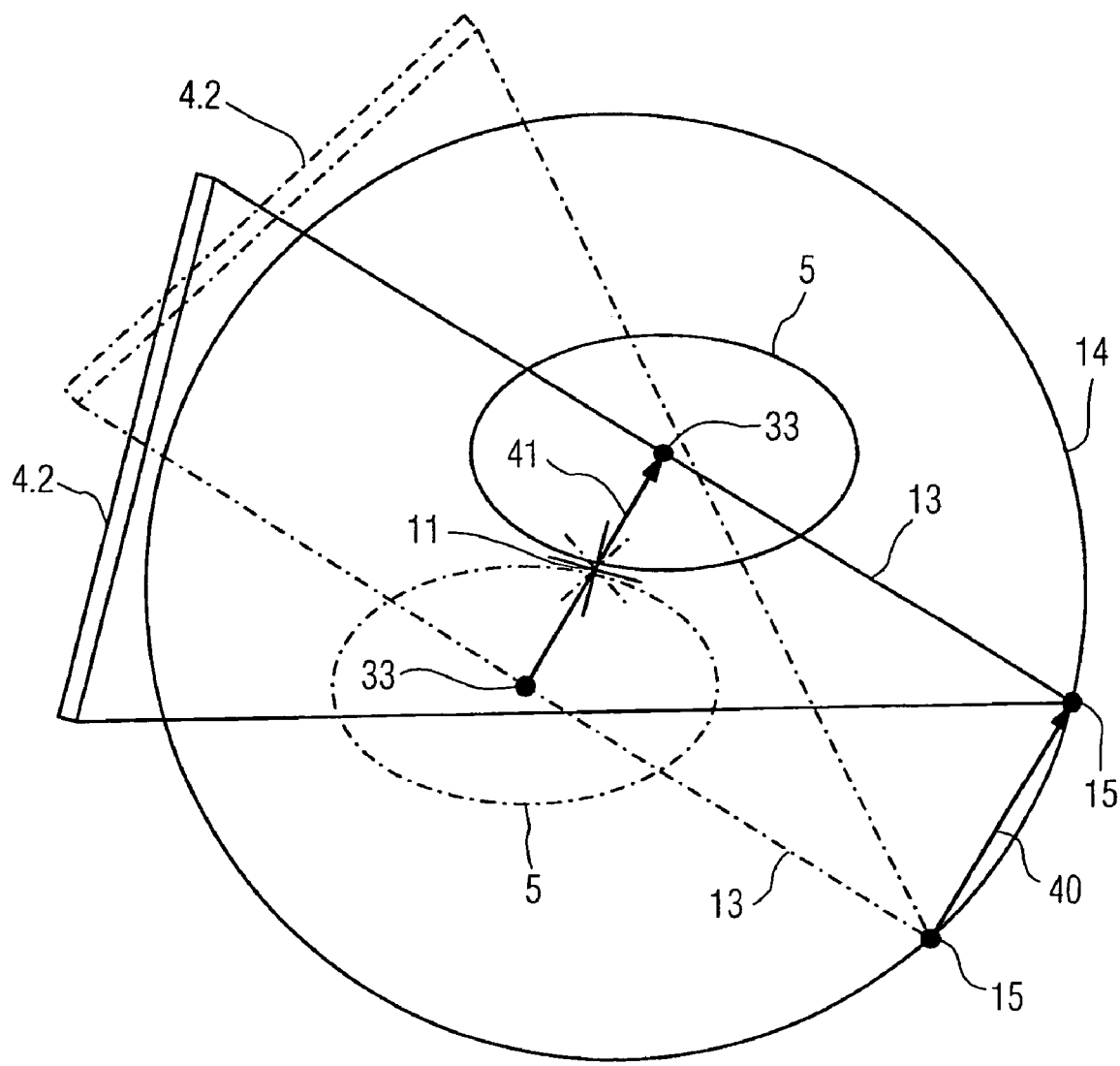
FIG. 19 shows a further projection geometry in the case of a movement both of the region of interest and also of the recording system between two individual projection images to be combined

The relative position between the focal point 15 and the region of interest 5 is the same in both positions; this means that a triangle, which is spanned by two arbitrarily selected fixed points in the region of interest 5 and the focal point 15, has the same size in the first position (first individual projection image) and the second position (second individual projection image). The geometric relations between the first and the second position are also as follows; if the region of interest 5 of the first position was made to cover the region of interest 5 of the second position, the recording system in the second position would result from a rotation of the recording system about the focal point 15. FIG. 19 similarly shows a first position (solid line) for recording a first individual projection image and a second position (dashed line) for recording a second individual projection image, with the first and the second projection then being able to be combined.

The third alternative is advantageous compared with the first alternative in that it can also be implemented with a conventional C-arm x-ray device, which can only be rotated about an axis of rotation 11, provided an adjustable patient bed is also available. Compared with the second alternative, said third alternative is advantageous in that a patient bed accommodating the region of interest 5 only needs to be moveable in a two-dimensional manner in the C-arm plane, but does not need to be tilted, thereby also simplifying the support of a patient.

Figure 20:
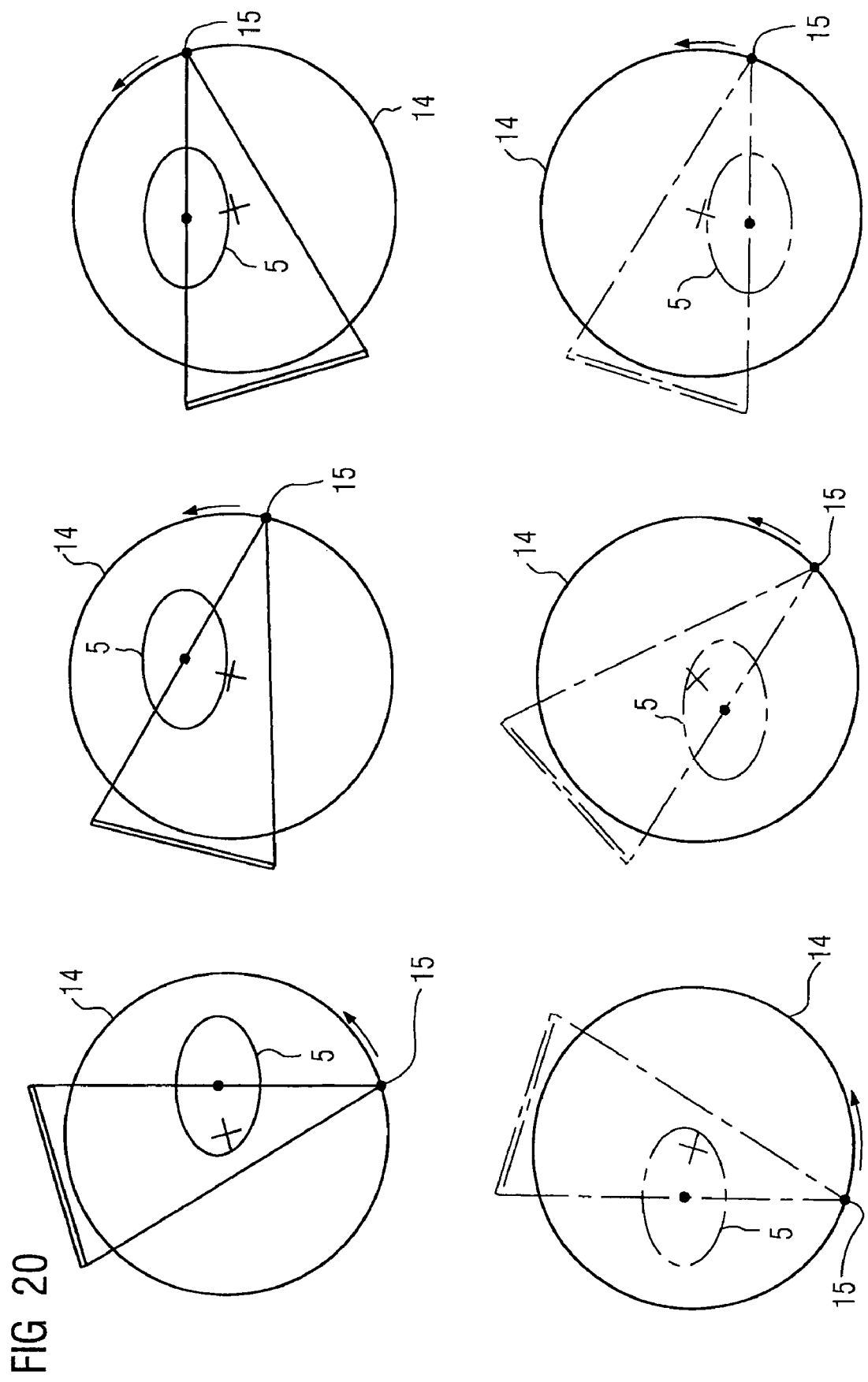
FIG. 20 shows a cutout from two rotational passes in the case of a movement both of the region of interest and also of the recording system between two individual projection images to be combined

FIG. 20 shows three cutouts from two rotational passes, with the recording sequence of the projection images here being such that all the first individual images are recorded first during a first rotational pass of the recording system about the region of interest (solid lines; top images), and all the second individual projection images are then recorded during a second rotational pass of the recording system about the region of interest (dashed lines; lower images), with each first projection image then being combined with a corresponding second projection image after recording. The rotational passes can amount to 360° or less for instance.

The recording sequence of the projection images can also be such that the respectively at least two individual projection images, which are combined to form an extended two-dimensional projection image in each instance, are recorded in direct sequence during an individual rotational pass of the recording system about the region of interest.

With the second and the third alternatives of the invention, the individual projection images to be combined with one another can also overlap or adjoin flush with one another.

To combine the at least two projection images to form an extended projection image, it is advantageous to set up a so-called virtual detector, with the virtual detector additionally describing the spatial position and arrangement of the recording system and object. Two methods can be used to set up the virtual detector, with the first method being implemented in a detector-based manner, in other words on the basis of the Cartesian arrangement of the detector matrix of the x-ray detector and the second method being implemented on a filter line-basis, in other words on the basis of the arrangement of filter lines.

Figure 21:
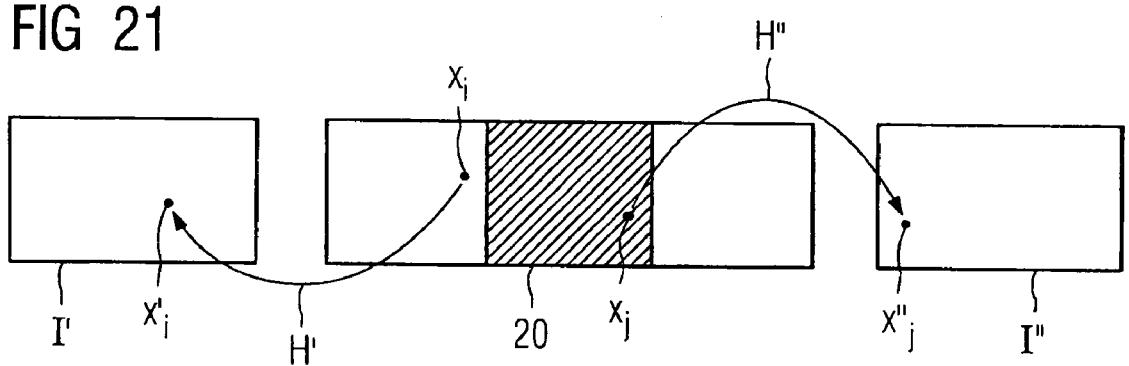
FIG. 21 shows a relation between the individual projection images and the virtual detector

The following relations are defined between the points $x_i$ and $x_j$ in the virtual detector 20, in other words in the combined extended projection image, and the points $x_i'$ and $x_j''$ in the first individual projection image I' and the second individual projection image I", by the homographies H' and H", in other words the first homography H' related to the first individual projection image I' and the second homography H" related to the second individual projection image I", as shown in FIG. 21:

$$x_i' = H' x_i \quad (a)$$

$$x_j'' = H'' x_j \quad (b)$$

Figure 23:
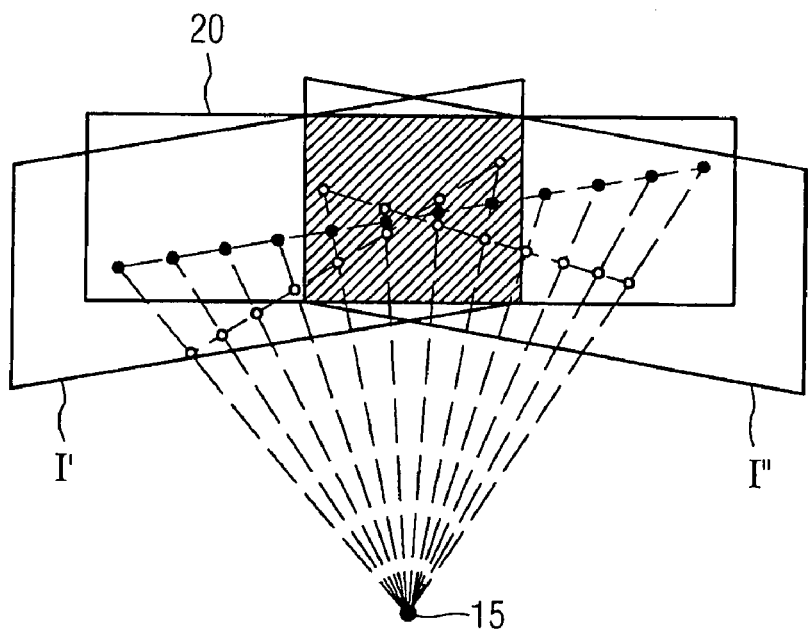
FIG. 23 shows a spatial representation of the filter line-based approach to setting up the virtual detector

With regard to the filtering to be implemented with FBP algorithms along lines in the detector, so-called filter lines, it may be expedient to set up the virtual detector in a 'filter line-based manner', based on the arrangement of the filter lines, and not in a 'detector-based' manner, based on the Cartesian arrangement of the detector matrix, since more recent reconstruction methods particularly define tilted filter lines (FIG. 23)

A filter line-based structure of the virtual detector is advantageous in that the values along the filter lines can be determined directly with the aid of the equations (a) and (b) from the first individual projection image I' and the second individual projection image I'', as a result of which subsequent interpolation of these values from the virtual detector 20 is avoided.

In contrast to the detector-based procedure, the filter line-based procedure can no longer be understood as an independent preprocessing step of the reconstruction, because the position of the filter lines needs to be included and this depends on the reconstruction algorithm. In the case of tilted filter lines, the filter line-based approach of the reconstruction however results in a reduced number of interpolations and may in many cases, both in respect of computing time and also the local resolution that can be achieved during reconstruction, be preferred to a detector-based procedure. With the FDK algorithm, filter line-based and detector-based procedures are equivalent, since the detector lines coincide with the filter lines here. The detector-based approach can thus be regarded as a special case of the filter line-based approach, with which the filter lines can come to lie on the detector grid.

The first and second homographies H' and H'' define the geometric relationship between the first projection image I' and the virtual detector 20 as well as between the second projection image I'' and the virtual detector 20—shown in FIG. 21. With the aid of the homographies H' and H'', the required gray scale values can be measured at the positions of the points $x_i'$ of the first projection image and $x_j''$ of the second projection image from the individual projection images I' and I''. In this way, the mappings $x_i$ and $x_j$ of the points $x_i'$ and $x_j''$ generally no longer come to lie on the detector grid, for which reason the gray scale values at these positions are determined from available adjacent values by means of interpolation, for instance bilinear interpolation. The overlap region of the individual projection images I' and I'' is shown by shading in the virtual detector 20.

Figure 22:
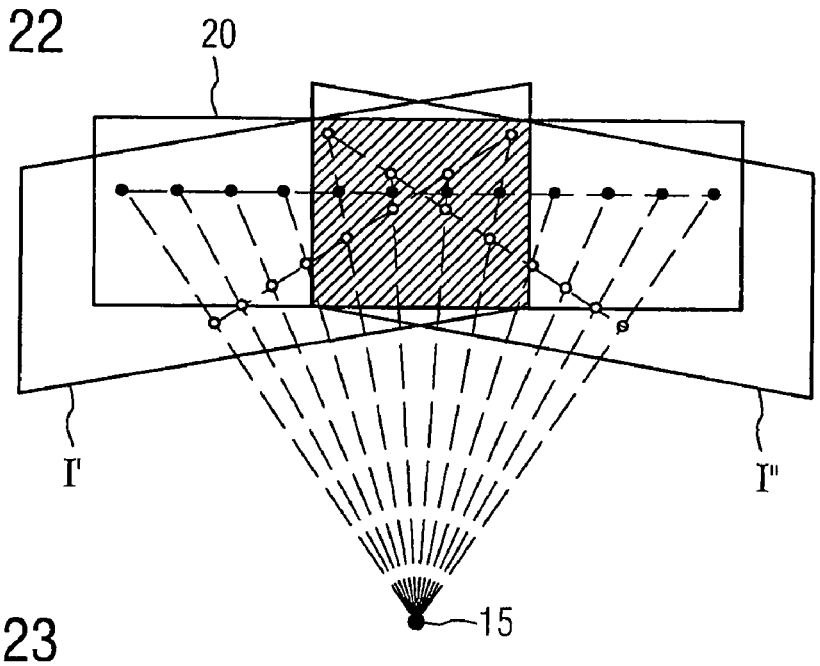
FIG. 22 shows a spatial representation of the detector-based approach to setting up the virtual detector

FIG. 22 shows a detector-based approach using the example of any arbitrary detector column and FIG. 23 shows a filter line-based approach using the example of any filter line. The black points each indicate the positions on the virtual detector 20, at which the gray scale values are determined by interpolation from the gray scale values of the individual projection images I' and I'', the hollow points indicate the positions on the respective individual projection images. In the overlap region of the first individual projection image I' with the second individual projection image I'' (shown shaded), a suitable interpolation strategy should be used, since gray scale values from both individual projection images are present here.

The symbolic connection of the points by dashed lines illustrates that the homographies H' and H'' map lines on lines again. (The distances between the points (and thus the scanning) along the lines nevertheless change). It is likewise obvious that the detector-based approach is a special case of the filter line-based approach, when filtering is carried out along horizontal lines.

The invention can be summarized briefly as follows: To enable an artifact free reconstruction even in the case of large regions of interest and with scanning paths of below 360°, provision is made for a method, with which a three-dimensional image volume is reconstructed from a number of two-dimensional projection images of a region of interest, which were recorded about the region of interest during a rotation of a recording system, comprising an x-ray source with a focal point and a detector, by calculating the gray scale values of the voxels of the image volume by back projection of the projection images, with which each two-dimensional projection images is composed in each instance from at least two individual projection images to form an extended two-dimensional projection image, with the respectively at least two individual projection images being recorded with a constant relative position between the focal point and the region of interest.

The invention claimed is:

1. A method for reconstructing a three-dimensional image volume of a region of interest of a patient, comprising:
   recording a plurality of individual two-dimensional projection images of the region of interest during a rotation of a recording system comprising an x-ray source and an x-ray detector with a constant relative position between a focal point of the x-ray source and the region of interest, the recording system being rotated about a first rotation center between the radiation source and the x-ray detector and simultaneously about a second rotation center in the focal point of the x-ray source;
   combining the individual two-dimensional projection images to produce a plurality of extend two-dimensional projection images of the region of interest by a control and computing unit; and
   reconstructing the three-dimensional image volume of the region of interest from the extend two-dimensional projection images with a reduced artifact by the control and computing unit for medically examining the patient.

2. The method as claimed in claim 1 wherein the individual projection images are different in that the focal point and the region of interest are positioned differently relative to one another with the constant relative position and the recording system is rotated differently about the focal point or about an axis of rotation through the focal point.

3. The method as claimed in claim 1, wherein the individual projection images are different in respect of an angle of rotation through which the recording system or the region of interest is rotated about the focal point or about an axis of rotation through the focal point while the focal point and the region of interest are fixed.

4. The method as claimed in claim 3, wherein the angle of rotation is arranged in a plane.

5. The method as claimed in claim 3, wherein the rotation of the recording system or the region of interest about the focal point lies in a rotation plane of the recording system about the region of interest.

6. The method as claimed in claim 1,
   wherein a first and a second individual projection images are recorded at a first and second angle of rotations of the recording system about the focal point or about an axis of rotation through the focal point, and
   wherein the first angle of rotation corresponds to a negative of the second angle of rotation.

7. The method as claimed in claim 1, wherein the individual projection images to be combined comprises an overlap relative to one another of more than 0% and less than 50% or 10%.

8. The method as claimed in claim 7, wherein the overlap is adjusted as a function of a size of the interest region.

9. The method as claimed in claim 1, wherein the individual projection images are recorded by recording all first individual projection images during a first rotational pass of the recording system about the region of interest and recoding all second individual projection images during a second rotational pass of the recording system about the region of interest.

10. The method as claimed in claim 1, wherein the individual projection images are recorded in a direct sequence during a single rotational pass of the recording system about the region of interest.

11. The method as claimed in claim 1, wherein an x-ray beam generated by the x-ray source is a cone or a fan beam.

12. The method as claimed in claim 1, wherein the individual projection images are combined by setting up a virtual detector based on Cartesian arrangement of a detector matrix of the x-ray detector or an arrangement of filter lines.

13. An x-ay device for reconstructing a three-dimensional image volume of a region of interest of a patient, comprising:
   a recording system comprising an x-ray source and an x-ray detector that records a plurality of individual two-dimensional projection images of the region of interest by rotating the recording system about a first rotation center between the x-ray source and the x-ray detector and simultaneously about a second rotation center in a focal point of the x-ray source; and
   a control and computing unit that:
      combines the individual two-dimensional projection images to produce an extend two-dimensional projection image, and
      reconstructs the three-dimensional image volume from the extend two-dimensional projection image with a reduced artifact.

14. The x-ray device as claimed in claim 13, wherein the individual projection images are recorded by recording all first individual projection images during a first rotational pass of the recording system about the region of interest and recoding all second individual projection images during a second rotational pass of the recording system about the region of interest.

15. The x-ray device as claimed in claim 13, wherein the individual projection images are recorded in a direct sequence during a single rotational pass of the recording system about the region of interest.

16. The x-ray device as claimed in claim 13, wherein the recording system is arranged on an articulated arm robot or industrial robot directly or by a bracket.

17. An x-ray device for reconstructing a three-dimensional image volume of a region of interest of a patient, comprising:
   a recording system comprising an x-ray source and an x-ray detector that records a plurality of individual two-dimensional projection images of the region of interest by rotating the recording system about a first rotation center between the radiation source and the x-ray detector;
   an adjustable patient support table that rotates the region of interest about a second rotation center in a focal point of the x-ray source; and
   a control and computing unit that:
      combines the individual two-dimensional projection images to produce an extend two-dimensional projection image, and
      reconstructs the three-dimensional image volume from the extend two-dimensional projection image with a reduced artifact.

18. The x-ray device as claimed in claim 17, wherein the individual projection images are recorded by recording all first individual projection images during a first rotational pass of the recording system about the region of interest and recoding all second individual projection images during a second rotational pass of the recording system about the region of interest.

19. The x-ray device as claimed in claim 17, wherein the individual projection images are recorded in a direct sequence during a single rotational pass of the recording system about the region of interest.

20. The x-ray device as claimed in claim 17, wherein the recording system is arranged on an articulated arm robot or industrial robot directly or by a bracket.

* * * * *